US00PP34924P3

(12) United States Plant Patent
Hand et al.

(10) Patent No.: US PP34,924 P3
(45) Date of Patent: Jan. 17, 2023

(54) ***CANNABIS* PLANT NAMED 'MOC20P01'**

(50) Latin Name: *Cannabis sativa*
Varietal Denomination: 'MOC20P01'

(71) Applicant: Aurora Cannabis Enterprises Inc., Vancouver (CA)

(72) Inventors: Andrew Hand, Comox (CA); Alan Graziano, Toronto (CA)

(73) Assignee: Aurora Cannabis Enterprises Inc.

( * ) Notice: Subject to any disclaimer, the term of this patent is extended or adjusted under 35 U.S.C. 154(b) by 0 days.

(21) Appl. No.: 17/214,694

(22) Filed: Mar. 26, 2021

(65) Prior Publication Data

US 2021/0307226 P1 Sep. 30, 2021

(30) Foreign Application Priority Data

Mar. 27, 2020 (CA) ..... 20-10130

(51) Int. Cl.
*A01H 5/02* (2018.01)
*A01H 5/12* (2018.01)
*A01H 6/28* (2018.01)

(52) U.S. Cl.
USPC ..... Plt./258
CPC ..... *A01H 6/28* (2018.05)

(58) Field of Classification Search
USPC ..... Plt./258, 263.1
CPC ... A01H 5/02; A01H 5/00; A01H 5/12; A01H 6/28
See application file for complete search history.

(56) References Cited

PUBLICATIONS https://online.plantvarieties.eu/publicConsultationDetails?registerId=20211751&denomination=MOC20P01&denominationFilter=contains; Nov. 17, 2021; 3 pages.*

* cited by examiner

*Primary Examiner* — Kent L Bell
(74) *Attorney, Agent, or Firm* — Christensen O'Connor Johnson Kindness PLLC

(57) ABSTRACT

A new cultivar of *Cannabis* plant named 'MOC20P01' that is characterized by about 1% THC and about 16% CBD by dry weight.

5 Drawing Sheets

Genus and species designation: *Cannabis sativa.*

Variety denomination: The varietal denomination of the claimed *Cannabis* (*Cannabis sativa*) cultivar is 'MOC20P01'.

CROSS-REFERENCE TO RELATED APPLICATION

This application claims the benefit of priority under 35 U.S.C. 199(f) to Canadian Plant Breeders' Rights Application Number 20-10130, which was filed for the instant plant variety on Mar. 27, 2020.

BACKGROUND

The present invention relates to a new and distinct *Cannabis* (*Cannabis sativa*) cultivar designated as 'MOC20P01'.

'MOC20P01' is a selection resulting from a controlled cross of female *Cannabis sativa* cultivar 'Nollia' (Buddha's Sister Seed #35, 'MOB19P01'; not patented) and male *Cannabis sativa* cultivar of uncertain background referred to as Med #1 Seed #1 (no agricultural ID; not patented). Crosses were made in June and September 2017, and the cultivar was first coned for flowering in March, 2018. The plants were grown in an indoor *Cannabis* facility in Markham, Ontario, Canada. The plants were flowered under standard indoor environment conditions with High Pressure Sodium (HPS) and light-emitting diode (LED) lamps with automatic ebb and flow irrigation.

Seeds from the cross were sown in the same facility in Markham, Ontario, Canada, and plants were screened for a number of traits including tetrahydrocannabinol (THC) and cannabidiol (CBD) levels, yield, flowering time, disease resistance, flower morphology, consistency, terpene content, and aroma. An individual plant was selected and named 'MOC20P01'.

In March 2018, 'MOC20P01' was first asexually propagated by apical stem cuttings approximately 10 cm long and having multiple auxiliary meristems, in Markham, Ontario, Canada. 'MOC20P01' is stable and reproduces true to type in successive generations of asexual reproduction. This cultivar produces high CBD levels, an increased CBD to THC ratio, which permits a relatively high production and extraction efficiency for CBD from a given growing environment.

SUMMARY

This invention relates to a new and distinctive *Cannabis* cultivar designated as 'MOC20P01'.

'MOC20P01' exhibits about 1% THC and 16% CBD by dry weight, a lack of observed disease issues, consistent batch characteristics, which ultimately permits highly efficient CBD production and extraction at scale.

DESCRIPTION OF THE DRAWINGS

The accompanying color photographs depict characteristics of 'MOC20P01' at about 11 weeks after rooting the clone. The photographs were taken in a facility in Saskatoon, Saskatchewan, Canada. The colors shown are as true as can be reasonably obtained by conventional photographic procedures.

DETAILED BOTANICAL DESCRIPTION

Figure 1:
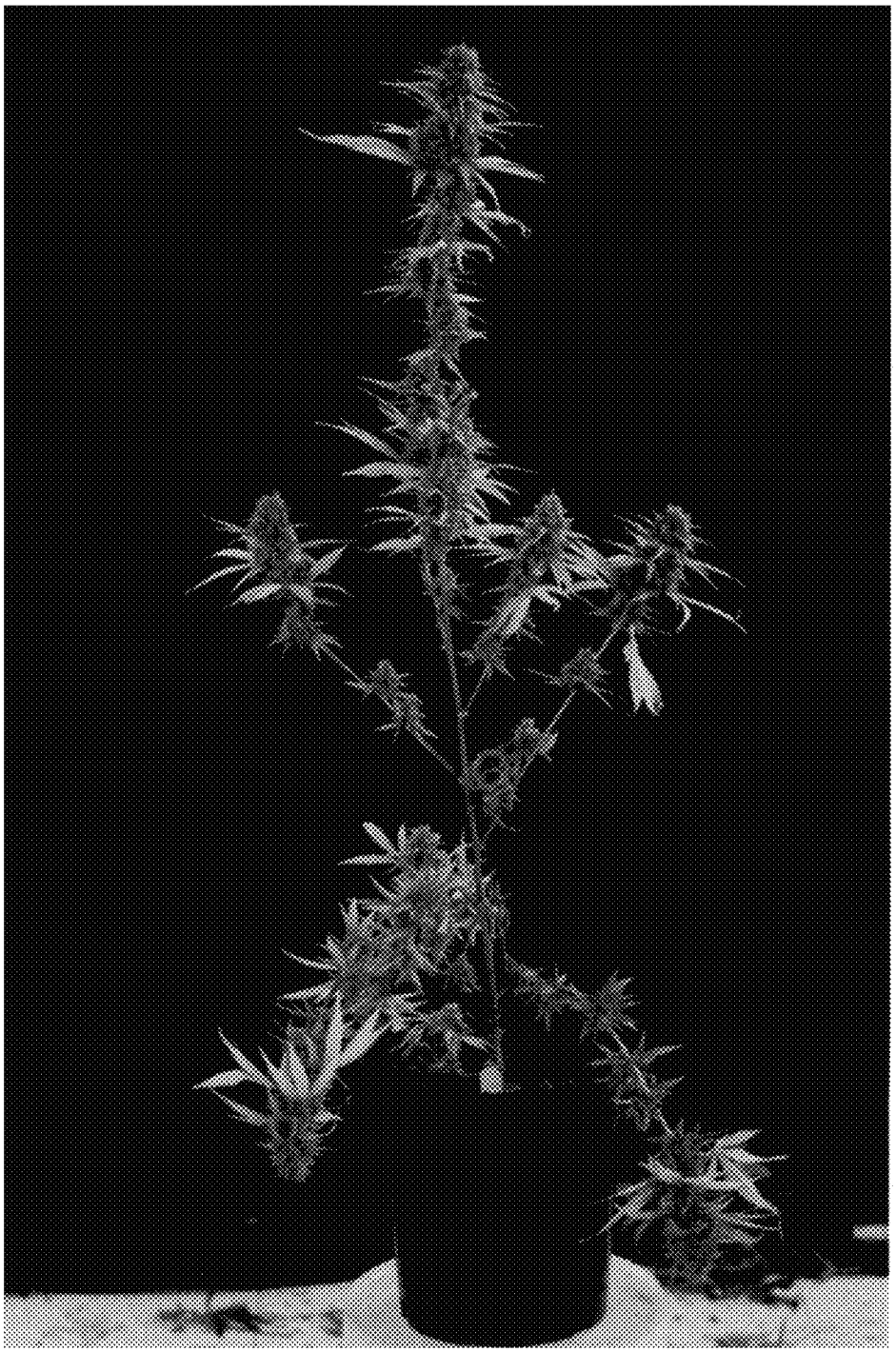
FIG. 1 shows a whole plant of 'MOC20P01'.
Figure 2:
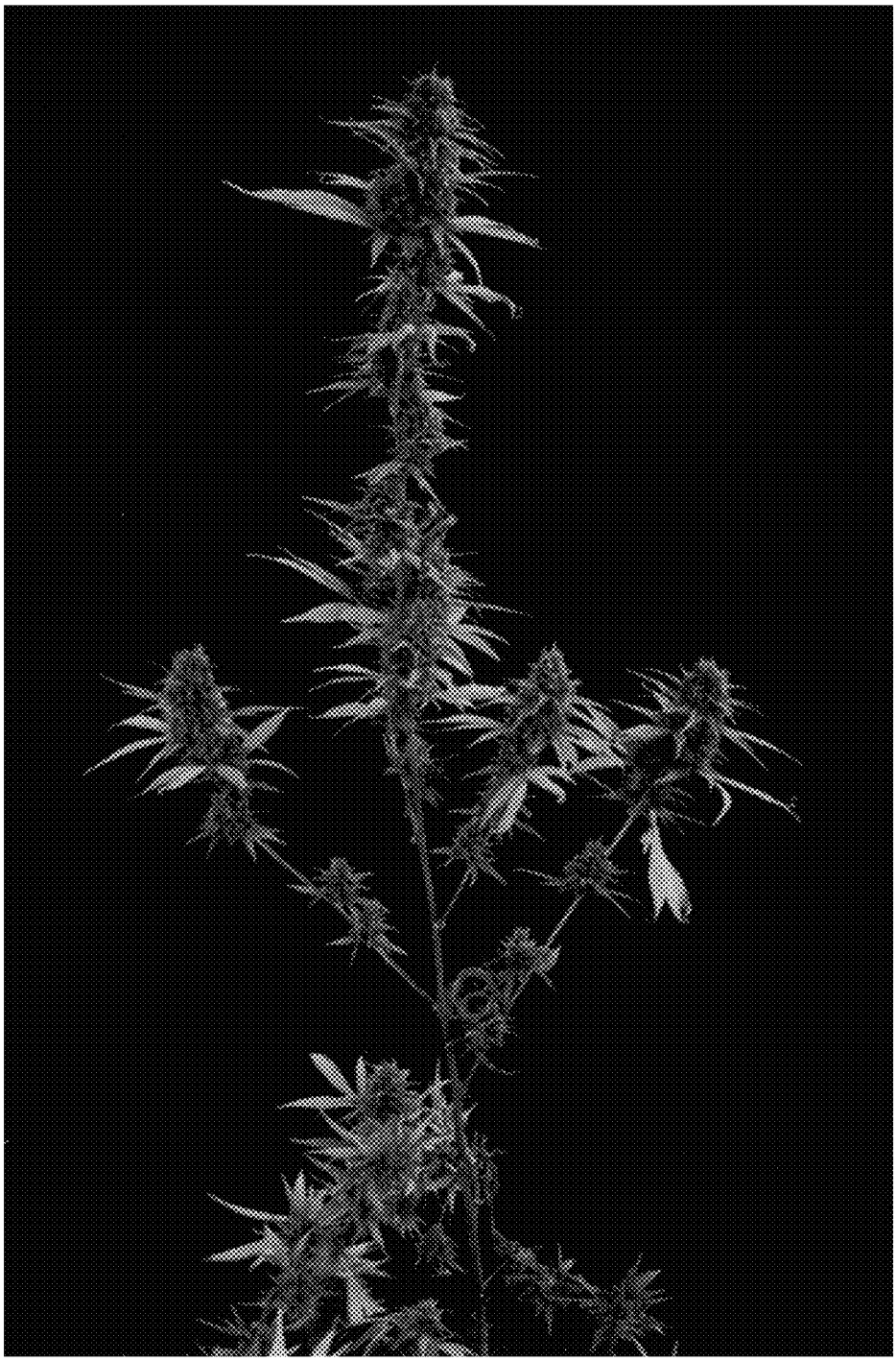
FIG. 2 shows a medium view of the stem, branches, inflorescence, and foliage of 'MOC20P01'.
Figure 3:
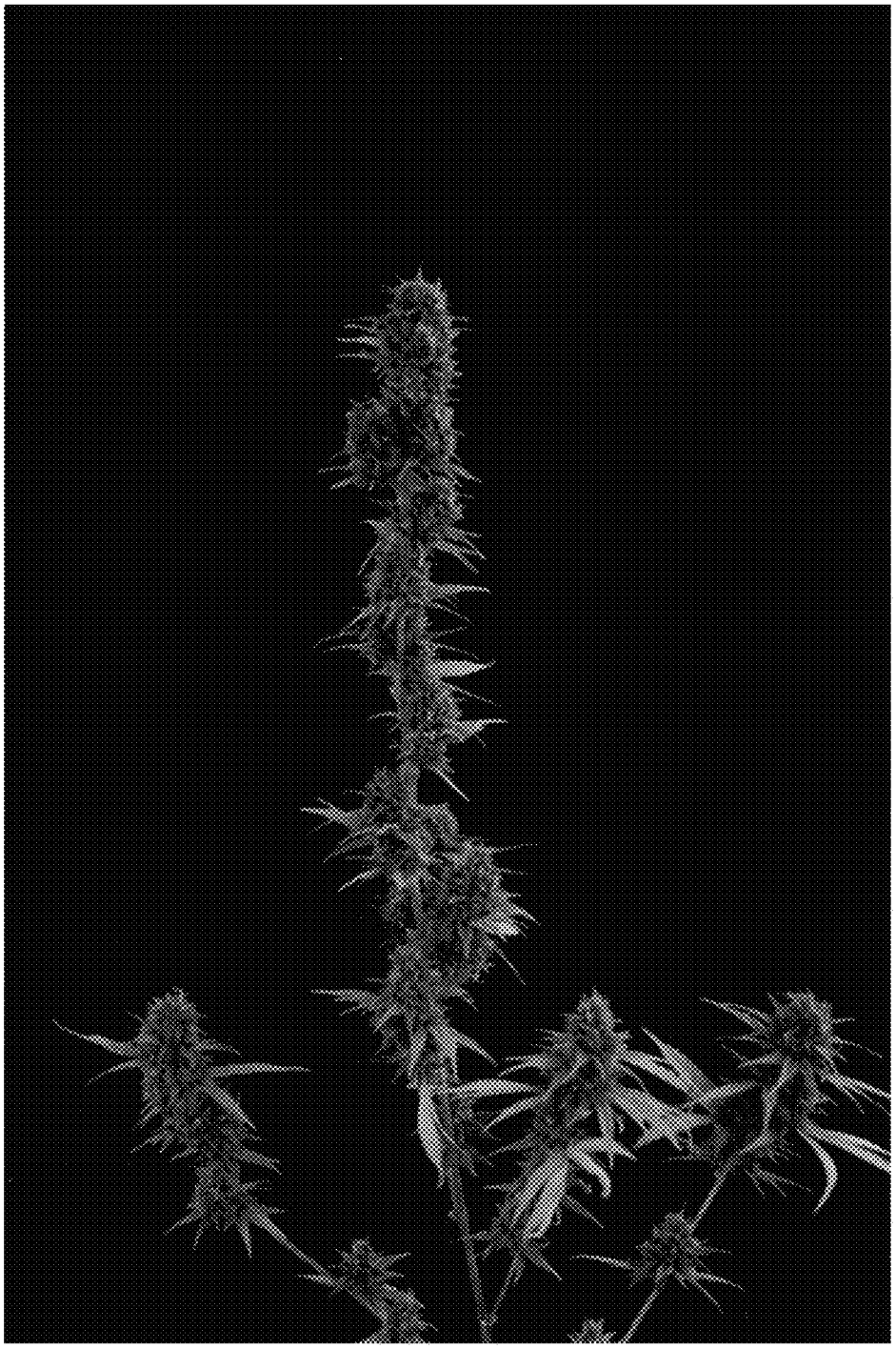
FIG. 3 shows an alternative medium view of the stem, branches, inflorescence, and foliage of 'MOC20P01'.
Figure 4:
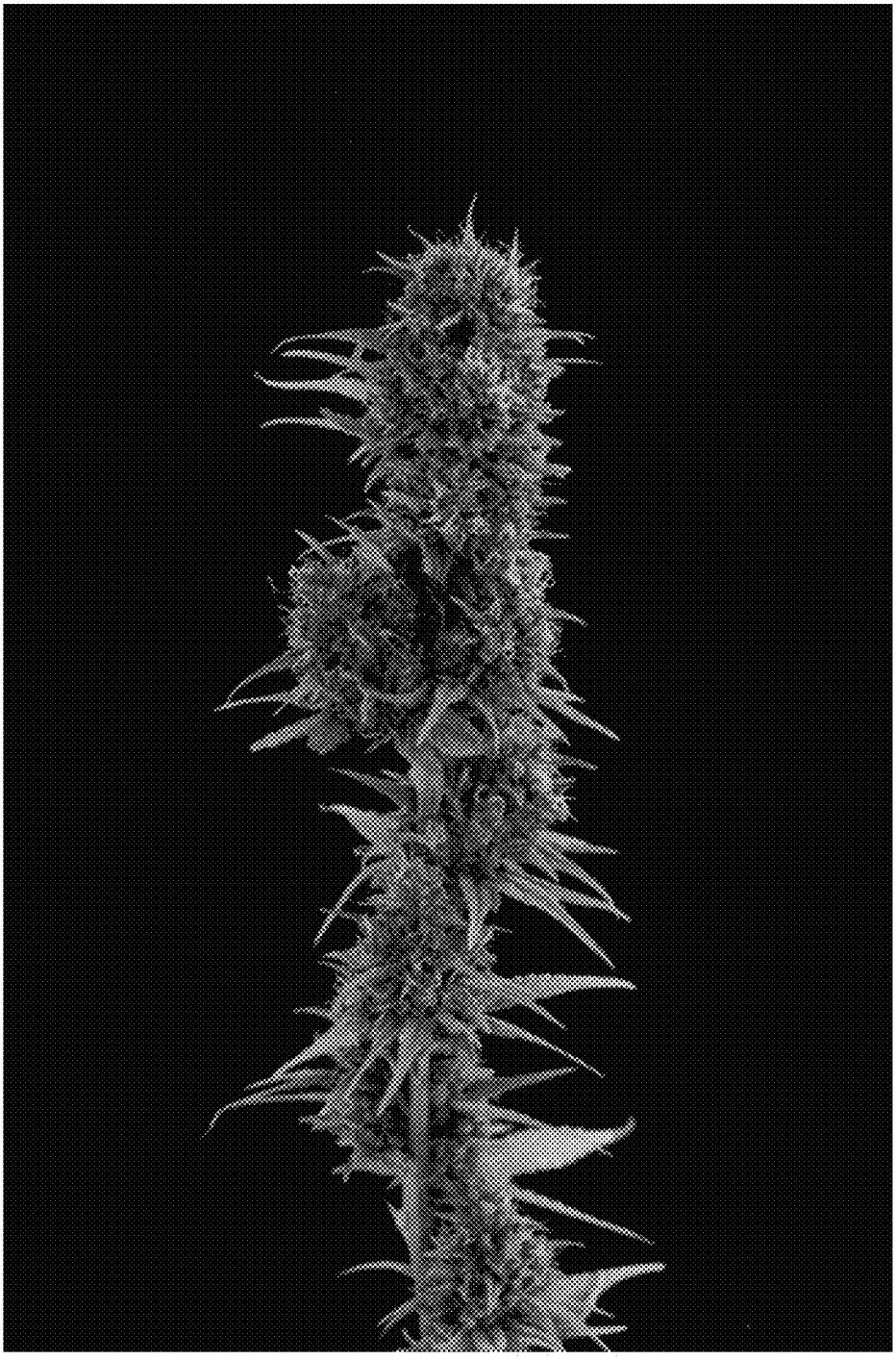
FIG. 4 shows a close-up view of an inflorescence and foliage of 'MOC20P01'.
Figure 5:
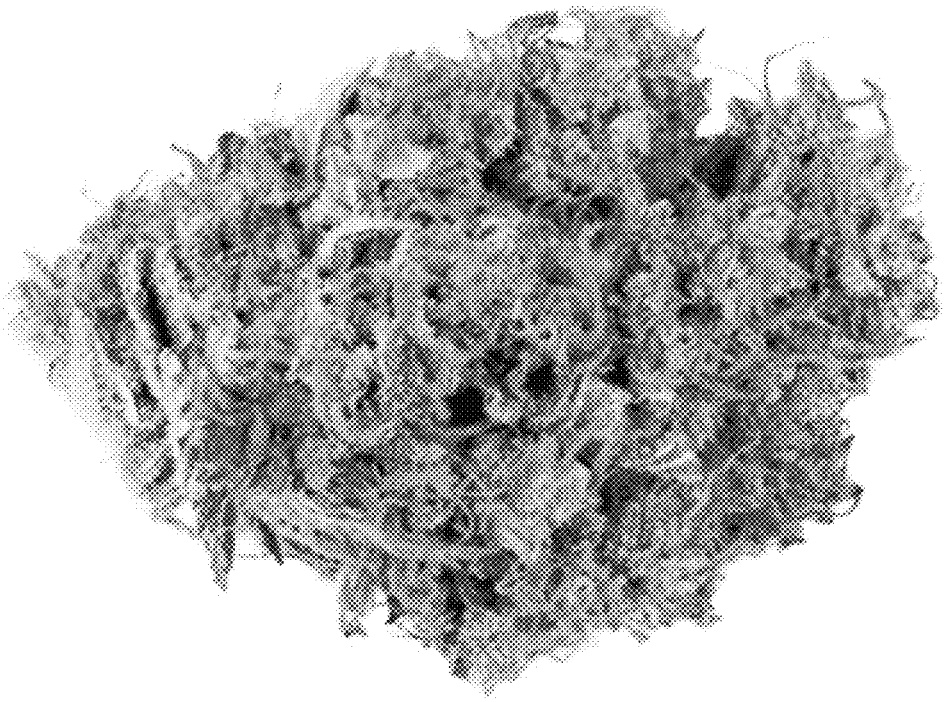
FIG. 5 shows a close-up view of a bud of 'MOC20P01'.

The following is a detailed description of the new cultivar 'MOC20P01'.

'MOC20P01' has not been tested under all possible environmental conditions. Phenotypic differences may be observed with variations in environment without any variance in genotype.

The traits of 'MOC20P01' have been repeatedly observed and represent the distinguishing characteristics of 'MOC20P01'.

The data that follows was collected in Markham, Ontario Canada.

Plants were flowered under standard indoor environmental conditions with High Pressure Sodium (HPS) and light-emitting diode (LED) lamps. Plants were cut from healthy mothers and allowed to root for 14 to 18 days prior to being introduced to the flower room. The room was maintained at 18 hour days/6 hour nights for a week to allow the cuttings to establish adequate vegetative tissue. The floral transition was initiated by switching to 12 hour days and 12 hour nights. Flowering lasted 8-9 weeks before harvest, at which point samples were taken for chemical analysis, and yield was quantified. Morphological measurements were taken from plants aged 9 weeks post-floral transition.

Standard in-house developed nutrients were used throughout growth, and the plants were defoliated and pruned as necessary throughout the cycle.

In the following description, the color determination is in accordance with the 2017 Munsell Plant Tissue Color Book, except where general color terms of ordinary dictionary significance are used.

Classification:

*Denomination*.—'MOC20P01'.
*Family*.—Cannabacaeae.
*Genus*.—*Cannabis*.
*Species*.—*Cannabis sativa*.
*Common name*.—Marijuana.

Parentage: Female *Cannabis sativa* variety 'Nollia' (Buddha's Sister Seed #35, 'MOB19P01') and male *Cannabis sativa* variety of uncertain background referred to as "Med #1 Seed #1" (no agricultural ID).

Propagation: 'MOC20P01' is asexually (clonally) propagated from vegetative cuttings. It takes approximately 14-18 days to produce a rooted young plant. Roots are fine and well-branched.

Plant:

*Height*.—79.5 cm-93.5 cm (average 86.5 cm).
*Diameter*.—35 cm-60 cm.

Stems:

*Length/height*.—79.5 cm-93.5 cm (average 86.5 cm).
*Width/diameter*.—8 mm-10 mm.
*Color*.—2.5 GY 5/6 [e.g., 2.5 GY 7/8, 5 RP 3/4].
*Shape*.—Tubular.
*Texture*.—Fibrous and Pubescent.
*Nodes*.—21-24 (average 23).

Foliage:

*Type/form*.—Palmately Compound.
*Arrangement*.—Alternate.
*Attachment*.—Petiolate.
*Leaf width*.—17 cm-20 cm.
*Leaf length*.—14 cm-16 cm.
*Number of leaflets per leaf*.—5-7.
*Leaflet shape*.—Lanceolate.
*Leaflet length*.—14 cm-16 cm.
*Leaflet width*.—2.5 cm-3 cm.
*Leaflet margin*.—Serrate.
*Leaflet apex*.—Acuminate.
*Leaflet base*.—Attenuate.
*Leaflet color, upper surface*.—7.5 GY 3/4.
*Leaflet color, lower surface*.—5 GY 5/4.
*Venation pattern and description, upper and lower leaflet surfaces*.—Pinnate.
*Texture (both surfaces)*.—Pubescent, primarily on the abaxial side and along leaf vasculature.
*Stipules*.—Present, 2 per node on either side of a petiole, attenuated.
*Fragrance*.—Earthy, herbal, tea aroma.

Petiole:

*Length*.—4 cm-6 cm.
*Diameter*.—~2 mm.
*Texture*.—Fine, short non-glandular trichomes.
*Color*.—5 GY 6/6, 5 RP 3/6.

Inflorescence: The plant is a genetically female dioicous plant and, therefore, produces predominantly female flowers. There are no male-only plants. There is a very low incidence of hermaphroditism.

*Blooming habit*.—Short day photoperiod sensitive.
*Blooming period*.—56 days (average) from photoperiod switch. Male flowering: male flowers are very rare and have not been observed.
*Attachment*.—Subsessile.
*Bracts*.—Covered with trichomes and resin glands with 2 stigmas.
*Bract shape*.—Slightly pointed at the apex; bracts ovate to lanceolate; margins entire; bases rounded to cuneate; apices acute to acuminate.
*Bract color*.—5GY 6/10 (exterior) and 5GY 5/6 (interior).
*Trichomes*.—Capitate-sessile, capitate-stalked, bulbous, and non-glandular (cystolith hairs); trichomes are present on almost all aerial organs but are present at highest concentration on female flowers (calyxes, bracts, etc.) as well as subtending intra-flower leaves.
*Bract trichome, resin gland color*.—Mix of mix of clear, cloudy, and 10R 4/8.
*Inflorescence color*.—5 GY 4/4.
*Number of inflorescences per plant*.—Approximately 23.
*Diameter*.—2.5 cm-5 cm.
*Length*.—3 cm-7 cm.
*Inflorescence anthocyanin*.—Absent for both female and male (very rare) flowers.
*Average flower width*.—4.4 cm.
*Inflorescence fragrance*.—Earthy, herbal, tea aroma.

Reproductive organs:

*Pistils.*—1.

*Quantity (of stigmas) per flower.*—2-2.

*Stigma length.*—0.3 cm-0.6 cm.

*Stigma width.*—<1 mm.

*Stigma color.*—2.5 GY 8/4, 7.5 YR 5/6, 10 R 3/4.

THC and CBD content: (As quantified with a Waters LC-MS/MS, running an Acetonitrile:Methanol:2-propanol gradient mobile phase through a Raptor ACR-18, 2.7 um, 2.1×150 mm column):

*Average % THC by dry weight.*—1%.

*Average % CBD by dry weight.*—13%-18% (average 16.2%).

Yield:

*Average flower yield.*—810 g/m$^2$ (grams dried, trimmed flower per m$^2$ of growing space).

*Average trim yield.*—170.1 g/m$^2$.

Disease and insect/pest resistance: Not directly tested. However, no disease or pest issues have been observed.

COMPARISON WITH KNOWN VARIETIES

When compared to female parental cultivar 'Nollia' (CBD: 5-8%; THC (3-5%)), 'MOC20P01' produces higher CBD and lower THC. 'MOC20P01' also yields significantly more mass than 'Nollia' (average of 378 g/m$^2$). 'Nollia' is also shorter than 'MOC20P01' at 70 cm on average. The male parent plant was not available for comparison.

A close variety of *Cannabis* known to the inventors is the commercial variety 'Avidekel' (not patented). The variety 'MOC20P01' can be distinguished from the variety 'Avidekel' by the traits shown in Table 1.

TABLE 1

Comparison between 'MOC20P01' and 'Avidekel'

| Characteristic | 'MOC20P01' | 'Avideke' |
|---|---|---|
| Overage Average Height | 86.5 cm | 49 cm |
| Average Active Height | 80.7 cm | 39 cm |
| Average # of Nodes | 23 | 26 |
| Average Yield (g/m$^2$) | 810 | 551 |
| Average Flower Width | 4.4 cm | 3.7 cm |
| Average % THC by Dry Weight | 1% | 0.55% |
| Average % CBD by Dry Weight | 13-18% | 12.44% |

In comparison to the variety 'Avidekel', the 'MOC20P01' variety is characterized as a high CBD producing cultivar. The 'MOC20P01' variety provides a high yield of CBD, which increases the grams CBD/m$^2$ growing space relative to other CBD-producing cultivars, such as the 'Avidekel' variety. This improvement allows for improved extraction efficiency. 'MOC20P01' propagates easily, grows consistently batch to batch, and had no observed disease issues to date, all of which promote production and extraction of CBD at scale.

The embodiments of the invention in which an exclusive property or privilege is claimed are defined as follows:

1. A new and distinct cultivar of *Cannabis* plant named 'MOC20P01' as described and illustrated herein.

* * * * *